United States Patent [19]
Uematsu et al.

[11] 3,993,771
[45] Nov. 23, 1976

[54] α-BENZYLIDENE LACTONE DERIVATIVES

[75] Inventors: Tamon Uematsu, Nishinomiya; Katsutoshi Tanaka, Funabashi, both of Japan; Yuzuru Sanemitsu, Darmstadt, Germany

[73] Assignee: Sumitomo Chemical Company, Limited, Osaka, Japan

[22] Filed: Apr. 22, 1975

[21] Appl. No.: 570,377

[30] Foreign Application Priority Data
Apr. 25, 1974 Japan................................. 49-47349

[52] U.S. Cl............................. 424/279; 260/240 R; 260/343.6
[51] Int. Cl.²........................................ C07D 307/58
[58] Field of Search..................... 260/240 R, 343.6; 424/279

[56] References Cited
UNITED STATES PATENTS
3,030,361  4/1962  Zimmer et al. ..................... 260/240

OTHER PUBLICATIONS
Zimmer, et al., J. Org. Chem. 29(4), 925–929 (1964).
Metzger, et al., Chem. Ber. 100(6), 1817–1823 (1967).
Takeda, et al., Chem. Abst. 69:86561t (1968).
Sakurai, et al., Yakugaku Zasshi 1968, 88 (7), 919–924.
Rioult, et al., Chem. Abst. 70:47197e (1969).
Wamhoff, et al., Chem. Abst. 71:29536f (1969).
Guyot, et al., Chem. Abst. 75:128973k.

*Primary Examiner*—Henry R. Jiles
*Assistant Examiner*—C. Jaisle
*Attorney, Agent, or Firm*—Wenderoth, Lind & Ponack

[57] ABSTRACT

The present invention relates to novel α-benzylidene-γ-butyrolactone derivatives and processes for the manufacture of them. Further, the present invention pertains to the fungicidal composition containing the same and use thereof.

11 Claims, No Drawings

α-BENZYLIDENE LACTONE DERIVATIVES

DESCRIPTION OF THE PRIOR ART

Some compounds similar to the present compounds are known. For example, Physiological Plant Vol. 2, 265 (1972), Yakugaku Sasshi Vol. 88, 919 (1968), J. Heterocyclic Chemistry Vol. 2, 95 (1965), Z. Naturforsch 24B, No. 5, 651 (1969), German Patent 844,292 and U.S. Pat. No. 2,993,891 disclose compounds which are very similar to the present compounds. But, as is clear from the comparative tests described hereinafter, it was found that the present compounds have an excellent fungicidal activity which can never be imagined from those of well-known compounds. The excellent activity and the excellent properties are due to the characteristic chemical structure of the present compounds.

SUMMARY OF THE INVENTION

One object of the present invention is to provide novel α-benzylidene-γ-butyrolactone derivatives having effective fungicidal activity. Another object of the present invention is to provide processes for manufacture of them and to provide fungicidal compositions thereof. Further object is apparent from the following descriptions.

In order to accomplish these objects the present invention provides a novel α-benzylidene-γ-butyrolactone of the general formula (I),

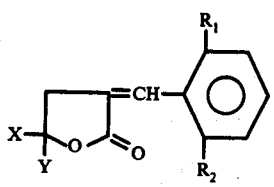

wherein $R_1$ and $R_2$ are, same or different, hydrogen, halogen or $C_1$–$C_4$ alkyl; X and Y are, same or different, hydrogen or $C_1$–$C_4$ alkyl; provided that both $R_1$ and $R_2$ are not hydrogen simultaneously, and $R_1$ and $R_2$ are not hydrogen and halogen respectively when both X and Y are hydrogen simultaneously.

In the present invention, a method for preparing the same is also provided, which comprises, A. condensing a γ-butyrolactone derivative of the formula (II),

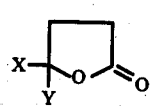

wherein X and Y are as defined above, with a benzaldehyde derivative of the formula (III),

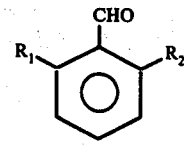

wherein $R_1$ and $R_2$ are as defined above,

B. reacting a butyrolactonylidene triphenylphosphorane derivative of the formula (IV),

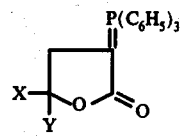

wherein X and Y are as defined above, with a benzaldehyde derivative of the formula (III),

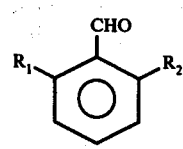

wherein $R_1$ and $R_2$ are as defined above,

C. condensing methylmalonic acid of the formula (V),

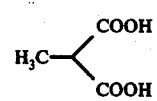

with benzaldehyde of the formula (III),

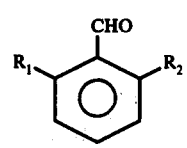

wherein $R_1$ and $R_2$ are as defined above, and then esterifying to obtain a compound of the formula (VI),

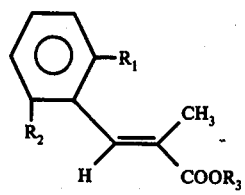

wherein $R_1$ and $R_2$ are as defined above, and $R_3$ is a $C_1$–$C_4$ alkyl group, and secondly, reacting the resulting compound (VI) with N-bromo-succinimide (NBS) to obtain a compound of the formula (VII),

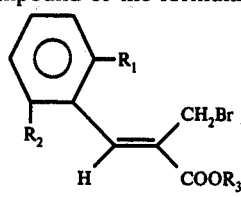

wherein $R_1$, $R_2$ and $R_3$ are as defined above, and lastly, reacting the resulting compound (VII) with zinc and a ketone or an aldehyde of the formula (VIII),

(VIII)

wherein X and Y are as defined above, in a suitable organic solvent such as benzene to obtain α-benzylidene-γ-butyrolactone derivatives of the formula (I), D. condensing an allylmalonic acid derivative of the formula (IX),

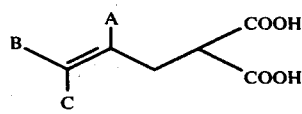
(IX)

wherein A, B and C are each hydrogen or $C_1$–$C_4$ alkyl, with a benzaldehyde derivative of the formula (III),

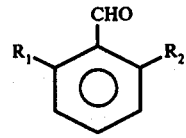
(III)

wherein $R_1$ and $R_2$ are as defined above, to obtain a compound of the formula (X),

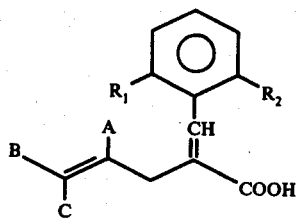
(X)

wherein A, B, C, $R_1$ and $R_2$ are as defined above, and then carrying out ring-closure of the resulting compound (X) in an acidic medium to obtain α-benzylidene-γ-butyrolactone derivatives of the formula (I), or (E) condensing a β,γ-unsaturated cyanide derivative of the formula (XI),

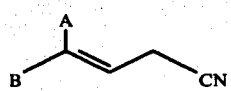
(XI)

wherein A and B are as defined above, with a benzaldehyde derivative of the formula (III),

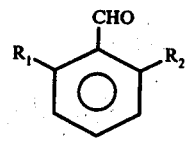
(III)

wherein $R_1$ and $R_2$ are as defined above, to obtain a compound of the formula (XII),

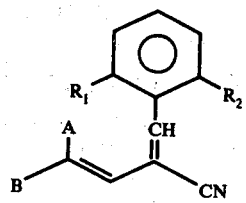
(XII)

wherein A, B, $R_1$ and $R_2$ are as defined above, and secondly, hydrolyzing the resulting compound (XII) in an acidic or alkaline medium to obtain a compound of the formula (XIII),

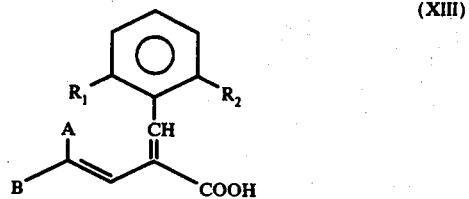
(XIII)

wherein A, B, $R_1$ and $R_2$ are as defined above, and lastly, carrying out ring-closure of the compound (XIII) in an acidic medium to obtain α-benzylidene-γ-butyrolactone derivatives of the formula (I).

In general, there are some well-known compounds among the γ-butyrolactone derivatives, but those which are found to have a biological activity against plant pathogens are very few, and moreover the practical effectiveness is hardly known. It was found that the compounds of the present invention have a strong and wide range of fungicidal activity which can never be imagined from other homologues thereof. That is, the α-benzylidene-γ-butyrolactone of which benzene nucleus was substituted at 2- and 6-positions with a $C_1$–$C_4$ alkyl group, a halogen or hydrogen atom (the two positions do not have hydrogen at the same time) and of which butyrolactone ring was substituted at γ-position with $C_1$–$C_4$ alkyl, or hydrogen, showed a prominent biological activity completely different from that of other homologues, that is, a stronger and wider range of fungicidal activity. Further surprisingly, there was found a new knowledge that the present compounds have an activity $10^2$ to $10^3$ times higher than that of control compounds without giving any perceptible side-effect on plant.

The compounds of the present invention have a wide range of controlling effect on rice blast, helminthosporium leaf spot and bacterial leaf blight of rice, brown rot of peach, gray mold and stem rot of agricultural and horticultural crops, ripe rot of grape, alternaria leaf spot and powdery mildew and blossom blight of apple, black spot of pear, damping-off of vegetables and citrus canker, and also can control two or more disease at the same time. Therefore, the present compounds are very superior as a fungicide against plant disease, particularly rice blast. Furthermore, the present compounds are very effective against propagation of molds on chemical products, and so they are also very superior as a fungicides for an industrial use. The present compounds are very low toxic and show only a very low toxicity to mammals and fishes.

The present invention was accomplished based on the above-mentioned new knowledge.

In the present invention, a preferred range of compounds is those which have the formula (I),

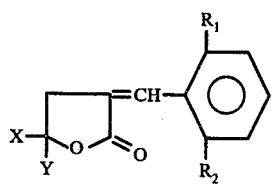

(I)

wherein $R_1$ is halogen and $R_2$, X and Y are as defined above.

Next, the methods according to the present invention will be illustrated in more details.

In the method (A) according to the present invention, a γ-butyrolactone derivative of the formula (II) is reacted with a benzaldehyde derivative of the formula (III) at a suitable temperature (for example, 0° to 120° C.) for 0.5 to 10 hours while stirring, in a suitable solvent (for example, benzene, toluene, xylene, tetrahydrofuran, dioxane, ether, dimethylformamide or a mixture thereof) in the presence of a suitable base (for example, potassium tert.-butylate, sodium methylate, sodium ethylate, sodium hydride, metallic sodium and metallic potassium). In this case, the reaction in a nitrogen gas atmosphere is preferred.

The reaction solution is then poured into water and acidified to pH of 6 to 1 with, for example, hydrochloric acid or sulfuric acid. At this stage, as some objective compounds are obtained as crystals, they are filtered and dried. Objective compounds which are not crystallized are extracted with a suitable organic solvent (for example, benzene, toluene, xylene, ether, ethyl acetate, chloroform or a mixture thereof), dried over a drying agent such as magnesium sulfate ($MgSO_4$), sodium sulfate ($Na_2SO_4$) or calcium chloride ($CaCl_2$), filtered and freed of the solvent under reduced pressure to obtain the objective compounds. These objective compounds can further be purified also by recrystallization, distillation of column chromatography.

In the method (B) according to the present invention, a γ-butyrolactonylidene triphenylphosphorane derivative of the formula (IV) is reacted with a benzaldehyde derivative of the formula (III) at a suitable temperature (for example, 0° to 120° C.) for 0.5 to 10 hours while stirring in a suitable solvent (for example, benzene, toluene, xylene, tetrahydrofuran, dioxane, ether, dimethylformamide or a mixture thereof).

On cooling the reaction solution, as some objective compounds are crystallized, they are filtered and dried. When objective compounds are not crystallized, the reaction solution is freed of the solvent under reduced pressure and the residue is dissolved in a water-insoluble solvent (for example, benzene, toluene, xylene, ether, chloroform, ethyl acetate or a mixture thereof), and then extracted with an aqueous alkali solution (for example, an aqueous sodium hydroxide or potassium hydroxide solution) having a pH of 8 to 12. The extract is acidified to pH of 6 to 1 with, for example, hydrochloric acid or sulfuric acid, and then extracted with a suitable organic solvent (for example, benzene, toluene, xylene, ether, chloroform, ethyl acetate or a mixture thereof). The extract is dried over a suitable drying agent such as magnesium sulfate ($MgSO_4$), sodium sulfate ($Na_2SO_4$) or calcium chloride ($CaCl_2$), filtered and freed of the solvent under reduced pressure to obtain the objective compounds. These compounds can further be purified also by recrystallization, distillation or column chromatography.

In the method (C) according to the present invention, methylmalonic acid of the formula (V) is reacted with a benzaldehyde derivative of the formula (III) at 0° to 120° C. for 0.5 to 100 hours in pyridine while stirring, in the presence of a suitable catalyst such as piperidine, dimethylamine or diethylamine. In this case, the reaction in a nitrogen gas atmosphere is preferred.

After the reaction, the reaction solution is poured into water and acidified to pH of 6 to 1 with, for example, hydrochloric acid or sulfuric acid. At this stage, as some compounds are obtained as crystals, they are filtered and dried. Compounds which are not crystallized are extracted with a suitable solvent (for example, benzene, toluene, xylene, ether, chloroform, ethyl acetate or a mixture thereof), dried over a suitable drying agent such as magnesium sulfate ($MgSO_4$), sodium sulfate ($Na_2SO_4$) or calcium chloride ($CaCl_2$), filtered and freed of the solvent under reduced pressure to obtain a cinnamic acid derivative.

The derivative thus obtained is esterified at 0° to 100° C. in a suitable alcohol (for example, methanol, ethanol, propanol or butanol) while stirring in the presence of as suitable acid catalyst such as hydrochloric acid, sulfuric acid, or p-toluenesulfonic acid, during which water formed is distilled off as an azeotropic mixture with, for example, benzene or toluene. Thereafter, the reaction solution is washed with water, dried over, for example, magnesium sulfate ($MgSO_4$) sodium sulfate ($Na_2SO_4$) or calcium chloride ($CaCl_2$) and freed of the solvent under reduced pressure to obtain the compound (VI).

The compound (VI) is reacted with N-bromosuccinimide (NBS) at 0° to 100° C. for 0.5 to 10 hours in a suitable solvent (for example, carbon tetrachloride ($CCl_4$), chloroform, benzene, toluene, xylene, tetrahydrofuran, dioxane or ether, and preferably carbon tetrachloride) while stirring. After the reaction, the reaction solution is filtered and freed of the solvent under reduced pressure to obtain the compound of formula (VII).

Then, the compound of formula (VII) is reacted with a ketone or an aldehyde of the formula (VIII) at 0° to 100° C. for 1 to 3 hours while stirring in a suitable solvent (for example, benzene, toluene, xylene, ether, tetrahydrofuran, dioxane or a mixture thereof) in the presence of zinc. Then, the reaction solution is acidified with, for example, hydrochloric acid or sulfuric acid, extracted with a suitable solvent (for example, benzene, toluene, xylene, chloroform, ether, ethyl acetate or a mixture thereof), dried over, for example, magnesium sulfate ($MgSO_4$), sodium sulfate ($Na_2SO_4$) or calcium chloride ($CaCl_2$), and then freed of the solvent under reduced pressure to obtain the objective compounds of formula (I). These compounds can further be purified also by recrystallization, distillation or column chromatography.

In the method (D) according to the present invention, allylmalonic acid of the formula (IX) is reacted with benzaldehyde of the formula (III) at a suitable temperature (for example, 0° to 120° C.) for a suitable period of time (for example, 0.5 to 100 hours) in pyridine while stirring, in the presence of a suitable catalyst (for example, piperidine, diethylamine or dimethylamine). In this case, the reaction in a nitrogen gas atmosphere is preferred.

The reaction solution is poured into water and acidified to pH of 6 to 1 with, for example, hydrochloric acid or sulfuric acid to obtain compounds of the formula (X). As some of compounds can be obtained as crystals, they are filtered and dried. Compounds which are not crystallized are extracted with a suitable solvent (for example, benzene, toluene, xylene, ether, chloroform or ethyl acetate), and the extract is then re-extracted solvent with an aqueous alkali solution (for example, an aqueous sodium hydroxide or potassium hydroxide solution) having a pH of 8 to 12. After the extraction, the alkali extract is acidified to pH of 6 to 1 with, for example, hydrochloric acid or sulfuric acid and then extracted with a suitable organic solvent (for example, benzene, toluene, xylene, ether, chloroform or ethyl acetate). The extract is dried over, for example, magnesium sulfate ($MgSO_4$), sodium sulfate ($Na_2SO_4$) or calcium chloride ($CaCl_2$), filtered and freed of the solvent under reduced pressure to obtain an α-benzylidene allylacetic acid derivative of the formula (X).

The derivative (X) thus obtained is heated at 50° to 200° C. for 0.5 to 5 hours in the presence of a suitable acid catalyst such as hydrochloric acid, sulfuric acid, formic acid, acetic acid, oxalic acid or a mixture thereof. To the reaction mass is added water, and the mixture is extracted with a suitable solvent (for example, benzene, toluene, xylene, ether, chloroform or ethyl acetate). The extract is dried over a suitable drying agent such as magnesium sulfate ($MgSO_4$), sodium sulfate ($Na_2SO_4$) or calcium chloride ($CaCl_2$), filtered and freed of the solvent under reduced pressure to obtain an α-benzylidene-γ-butyrolactone derivative of the formula (I). The derivative can further be purified also by recrystallization, distillation or column chromatography.

In the method (E) according to the present invention, a β,γ-unsaturated cyanide derivative of the formula (XI) is reacted with a benzaldehyde derivative of the formula (III) at 0° to 100° C. for 0.5 to 12 hours while stirring in a suitable solvent (for example, benzene, toluene, xylene ethanol, methanol, tert.-butanol, ether, dioxane, tetrahydrofuran, dimethylformamide or a mixture thereof), in the presence of a suitable base (for example, sodium methylate, sodium ethylate, metallic sodium, potassium tert.-butylate, metallic potassium, potassium hydroxide or sodium hydroxide).

Then, the reaction solution is poured into water, acidified to pH of 6 to 1 with a suitable acid such as hydrochloric acid or sulfuric acid, and then extracted with a suitable organic solvent (for example, benzene, toluene, xylene, ether, chloroform, ethylacetate or a mixture thereof). The extract is dried over a suitable drying agent such as magnesium sulfate ($MgSO_4$), sodium sulfate ($Na_2SO_4$) or calcium chloride $CaCl_2$), filtered and freed of the solvent under reduced pressure to obtain the compound of formula (XII).

The compound (XII) thus obtained is treated at 0° to 200° C. for 1 to 10 hours while stirring in a suitable solvent (for example, water, benzene, toulene, xylene, tetrahydrofuran or a mixture thereof), in the presence of a suitable acid catalyst (for example, hydrochloric acid, sulfuric acid, oxalic acid or formic acid) or a suitable alkali catalyst (for example, potassium hydroxide or sodium hydroxide).

The reaction solution is poured into water, acidified to pH of 6 to 1 with, for example, hydrochloric acid or sulfuric acid and extracted with a suitable solvent (for example, benzene, toluene, xylene, ether, chloroform, ethyl acetate or a mixture thereof). The extract is dried over a suitable drying agent such as magnesium sulfate ($MgSO_4$), sodium sulfate ($Na_2SO_4$) or calcium chloride ($CaCl_2$), filtered and freed of the solvent under reduced pressure to obtain a compound of the formula (XIII).

The compound (XIII) thus obtained is heated at 50° to 200° C. for 0.5 to 5 hours in the presence of a suitable acid catalyst such as hydrochloric acid, sulfuric acid, oxalic acid, acetic acid, formic acid or a mixture thereof. To the reaction mass is added water, and the mixture is extracted with a suitable solvent (for example, benzene, toluene, xylene, ether, chloroform or ethyl acetate). The extract is dried over a suitable drying agent such as magnesium sulfate ($MgSO_4$), sodium sulfate ($Na_2SO_4$) or calcium chloride ($CaCl_2$) and freed of solvent under reduced pressure to obtain the present compounds of the formula (I). These compounds can further be purified also by recrystallization, distillation or column chromatography.

The present invention will be illustrated in more details with reference to the following examples. But it is a matter of course that the present compounds, starting materials, reaction conditions are use of the present compounds are not limited to the examples but can be changed within a wide range.

EXAMPLE 1 (METHOD A)

To a suspension of 2.7 g. of sodium methylate and 5.7 g. of γ-dimethyl-γ-butyrolactone in 50 ml. of benzene were added dropwise, while stirring, 6.0 g. of o-methylbenzaldehyde under ice cooling. Thereafter, the reaction solution was stirred at room temperature for 3 hours, and then acidified with sulfuric acid. The crystals separated were filtered, washed with water and dried to obtain the objective α-(o-methylbenzylidene)-γ-dimethyl-γ-butyrolactone. Yield 90%, and m.p. 90° – 92° C.

Elementary analysis:

|  | C (%) | H (%) |
|---|---|---|
| Calculated (as $C_{14}H_{16}O_2$) | 77.73 | 7.47 |
| Found | 77.91 | 7.25 |

EXAMPLE 2 (METHOD B)

In a four-necked flask were charged 10.0 g. of γ-butyrolactonylidene triphenylphosphorane, 4.5 g. of 2,6-dichlorobenzaldehyde and 20 ml of tetrahydrofuran, and the mixture was stirred under reflux for 3 hours. Thus, the objective α-(2,6-dichlorobenzylidene)-γ-butyrolactone was obtained. Yield 88%, and $N_D^{28.0}$ 1.5932.

Elementary analysis:

|  | C (%) | H (%) | Cl (%) |
|---|---|---|---|
| Calculated (as $C_{11}H_8O_2Cl_2$) | 54.35 | 3.32 | 28.25 |
| Found | 54.31 | 3.38 | 28.29 |

EXAMPLE 3 (METHOD C)

In 30 ml of pyridine were dissolved 5.9 g. of methylmalonic acid, 7.0 g. of o-chlorobenzaldehyde and 4.7 g. of piperidine, and the resulting solution was heated at 100° C. for 8 hours. The reaction solution was poured into a 10% hydrochloric acid and separated crystals were filtered, washed with water and dried.

After methyl-esterification of the crystals obtained, the resulting compound was boiled for 2 hours together with an equimolar amount of N-bromosuccinimide in 50 ml. of carbon tetrachloride. The reaction solution was filtered, freed of carbon tetrachloride under reduced pressure to obtain the bromo-derivative.

The derivative thus obtained was boiled, while vigorously stirring, together with equimolar amounts of propionaldehyde and zinc granules in 30 ml. of benzene. The reaction solution was acidified with a 10% hydrochloric acid and the benzene layer was separated, dried and freed of the solvent under reduced pressure to obtain the objective α-(o-chlorobenzylidene)-γ-ethyl-γ-butyrolactone.

Yield 64.5%, and m.p. 38° – 39° C.
Elementary analysis:

|  | C (%) | H (%) | Cl (%) |
|---|---|---|---|
| Calculated (as $C_{13}H_{13}O_2Cl$) | 65.96 | 5.55 | 14.98 |
| Found | 66.32 | 5.29 | 14.99 |

EXAMPLE 4 (METHOD D)

In 50 ml. of pyridine were dissolved 7.2 g. of allylmalonic acid, 7.0 g. of o-chlorobenzaldehyde and 4.25 g. of piperidine, and the solution was stirred at 50° C. for 10 hours in a nitrogen gas atmosphere. Thereafter, the reaction solution was poured into 500 ml. of water and acidified to a pH of 1 with hydrochloric acid. Crystals separated were filtered, washed with water and dried.

The crystals were heated at 100° C. for 3 hours together with formic acid of 1.5 time by mole based thereon, and then the reaction mixture was shaken in benzene-water. The benzene layer was separated, washed with water, dried over sodium sulfate ($Na_2SO_4$), filtered and freed of benzene under reduced pressure to obtain the objective α-(o-chlorobenzylidene)-γ-valerolactone. Yield 92%, and m.p. 48° C.

Elementary analysis:

|  | C (%) | H (%) | Cl (%) |
|---|---|---|---|
| Calculated (as $C_{12}H_{11}O_2Cl$) | 64.74 | 4.99 | 15.92 |
| Found | 64.69 | 4.98 | 15.99 |

EXAMPLE 5 (METHOD E)

A solution of 400 mg. of metallic sodium in 17 ml. of ethanol was added to a solution of 4.5 g. of crotylcyanide and 8.8 g. of 2-chloro-6-fluorobenzaldehyde in 30 ml. of ethanol. The resulting solution was stirred at room temperature for 2 to 3 minutes, boiled for 1 minute and then allowed to stand for 8 hours in a refrigerator (0° to 3° C.). Thereafter, the solution was acidified with a 10% hydrochloric acid and extracted with benzene. The extract was dried over sodium sulfate ($Na_2SO_4$), filtered and freed of benzene under reduced pressure to obtain crystals.

The crystals was kept at 150° C. for 5 hours together with sodium hydroxide of 1.5 time by mole based thereon in 50 ml. of ethylene glycol. After cooling, the solution was acidified with a 20% hydrochloric acid, stirred for 1 hour and then extracted with benzene. The extraction was washed with water, dried over sodium sulfate, filtered and freed of benzene under reduced pressure. Thus, the objective α-(2-chloro-6-fluorobenzylidene)-γ-valerolactone was obtained. Yield 90.5%, and $n_D^{28.0}$ 1.5631.

Elementary analysis:

|  | C (%) | H (%) | Cl (%) |
|---|---|---|---|
| Calculated (as $C_{12}H_{10}O_2ClF$) | 59.88 | 4.20 | 14.73 |
| Found | 60.15 | 4.01 | 14.55 |

Typical examples of the present compound obtained by the above-mentioned methods are shown in Table 1, but the compounds of the present invention are of course not limited thereto.

Table 1

| Compound No. | Chemical formula | Physical constant | Method |
|---|---|---|---|
| (1) | 3-(2-methylbenzylidene)-dihydrofuran-2(3H)-one | m.p. 55–56° C. | E |
| (2) | 3-(2,6-dichlorobenzylidene)-dihydrofuran-2(3H)-one | $n_D^{28}$ 1.5932 | B |
| (3) | 3-(2-chloro-6-fluorobenzylidene)-5-methyl-dihydrofuran-2(3H)-one | $n_D^{28}$ 1.5631 | E |
| (4) | 3-(2,6-dimethylbenzylidene)-5-methyl-dihydrofuran-2(3H)-one | m.p. 23–26° C. | B |
| (5) | 3-(2-methylbenzylidene)-5-methyl-dihydrofuran-2(3H)-one | m.p. 48–49° C. | B |
| (6) | 3-(2-chlorobenzylidene)-5-methyl-dihydrofuran-2(3H)-one | m.p. 48° C. | D |
| (7) | 3-(2-bromobenzylidene)-5-methyl-dihydrofuran-2(3H)-one | m.p. 47–47.5° C. | B |
| (8) | 3-(2,6-dichlorobenzylidene)-5-methyl-dihydrofuran-2(3H)-one | $n_D^{25}$ 1.5712 | B |
| (9) | 3-(2-chlorobenzylidene)-5-ethyl-dihydrofuran-2(3H)-one | m.p. 38–39° C. | C |
| (10) | 3-(2-chlorobenzylidene)-5-tert-butyl-dihydrofuran-2(3H)-one | m.p. 99–100° C. | C |

Table 1-continued

| Compound No. | Chemical formula | Physical constant | Method |
|---|---|---|---|
| (11) | [structure: CH₃, CH₃, O, =CH-phenyl-Cl] | m.p. 131° C. | A |
| (12) | [structure: CH₃, CH₃, O, =CH-phenyl-CH₃] | m.p. 90–92° C. | A |
| (13) | [structure: isopropyl, O, CH₃, =CH-phenyl] | $n_D^{24.6}$ 1.5659 | B |
| (14) | [structure: Et, O, CH₃, =CH-phenyl] | $n_D^{25.0}$ 1.5021 | B |

The present compounds are shown hereinafter with the respective compound numbers.

On the practical application of the present compounds, they can be used alone without adding any other component, or in combination with solid or liquid carriers for the case of use as fungicides, for example in common preparation forms such as dusts, wettable powders, oil sprays, aerosols, tablets or granules. The composition according to the present invention can contain, as an active ingredient, 0.1 to 99.9% by weight of the compound of formula (I).

Furthermore, the present compounds can be applied in combination with other chemicals, for example Blasticiden-S, Kasugamycin, Polyoxin, Cellocidin, Griseofluvin, pentachloronitrobenzene, 4,5,6,7-tetrachlorophthalide, pentachlorophenol, pentachlorobenzyl alcohol, 2,6-dichloro-4-nitroaniline, zinc ethylene-bis-dithiocarbamate, manganous ethylene-bisdithiocarbamate, 2,3-dichloro-1,4-naphthoquinone, 2,4-dichloro-6-(o-chloroanilino)-S-triazine, 6-methyl-2,3-quinoxaline-dithiol cyclic-S,S-dithiocarbonate, N-(3,5-dichlorophenyl)-maleimide, N-(3,5-dichlorophenyl)-succinimide, 3-(3',5'-dichlorophenyl)-5,5-dimethyl oxazolidine-2,4-dione, N-(n-butylcarbamoyl)-2-methoxycarbonylamino-benzimidazole, O-ethyl-S,S-diphenylphosphorodithioate, O-butyl-S-benzyl-S-ethyl-phosphorodithioate, O,O-dimethyl-O-(3-methyl-4-nitrophenyl)-phosphorothioate, S-[1,2-bis(ethoxycarbonyl)ethyl]O,O-dimethylphosphorodithioate, O,O-diethyl-O-(2-isopropyl-6-methyl-4-pyrimidyl)-thio-phosphate, 3,4-dimethylphenyl-N-methylcarbamate, iron methylarsonate, 2,4-dichlorophenoxy acetic acid (including salts and esters thereof), 2-methyl-4-chlorophenoxy acetic acid (including salts and esters thereof), 2,4-dichlorophenyl-4'-nitrophenylether, 1-naphthyl N-methylcarbamate, methyl N-(3,4-dichlorophenyl)-carbamate, 4-chlorobenzyl N,N-dimethylthiocarbamate, cyclohexyl β-(2,4-dichlorophenoxy)-acrylate.

In these cases, since each active ingredient in the mixed preparations does not reduce its controlling effect, a simultaneous controlling effect on two or more kinds of injurious insect can be obtained. Furthermore, the present compounds can also be used in combination with agricultural chemicals such as namatocides and acaricides, or fertilizers.

Next, preparation examples of the present fungicides will be given.

Preparation Example
1. Dust

Three parts of the compound (1) and 97 parts of clay were thoroughly blended and comminuted to obtain a dust containing 3% active ingredient. In practical use, the dust thus obtained can be employed as it is or can be used for coating seeds.

2. Dust

Two parts of the compound (6) and 98 parts of clay were thoroughly blended and comminuted to obtain a dust containing 2% active ingredient. In practical use, the dust thus obtained can be employed per se or can be blended with soil prior to the application.

3. Wettable powder

Thirty five parts of the compound (13), 5 parts of a spreading agent (alkylbenzene sulfonic acid salt type) and 60 parts of diatomaceous earth were thoroughly blended and comminuted to obtain a wettable powder containing 35% active ingredient. Application can be by spraying or dipping in the form of dilute aqueous solution.

4. Emulsifiable concentrate

Fifty parts of compound (10), 40 parts of dimethylsulfoxide and 10 parts of an emulsifier (a polyoxyethylene phenylphenol ether type) were mixed well to obtain an emulsifiable concentrate containing 50% of the active ingredient. Application can be by using as it is, or by spraying in the form of an aqueous dilute solution.

5. Granules

Five parts of compound (4), 93.5 parts of clay and 1.5 parts of a binding agent (a polyvinyl alcohol type) were well ground and kneaded with water, granulated and dried to obtain granules containing 5% of the active ingredient. Direct application of the granules can be employed.

6. Mixed dust

Two parts of compound (1) 3 parts of O,O-dimethyl-O-(3-methyl-4-nitrophenyl)phosphorothioate and 95 parts of clay were mixed while powdering to obtain a mixed dust containing 5% of the active ingredients. Application can be by dusting as it is.

7. Mixed wettable powder

Thirty parts of compound (10), 20 parts of 2,3,4,5-tetrachloro-phthalide, 5 parts of calcium alkylbenzene sulfonate (a wetting agent) and 45 parts of diatomaceous earth were mixed while powdering to obtain a mixed wettable powder containing 50% of the active ingredients. Application can be by spraying or dipping in the form of dilute aqueous solution.

Next, the fact that the α-benzylidene-γ-butyrolactone derivatives according to the present invention are extremely superior in a fungicidal activity to the well-known compounds and homologues will be demonstrated in more details with reference to the examples, which are not however limited thereto. Compounds which were used as a control in the examples are as shown in Table 2.

Table 2

| Compound No. | Chemical formula | Remarks |
|---|---|---|
| (i) | =CH$_2$ b.p. 53–60° C/0.45 mmHg | Physiological Plant pathology Vol. 2, 265 (1972) |
| (ii) | =CH—〇 m.p. 113–115° C. | Yakugaku Zasshi Vol. 88, 919 (1968) |
| (iii) | =CH—〇—OH m.p. 183–184° C. | U.S. Pat. No. 2,993,891 |
| (iv) | =CH—〇—OCH$_3$ m.p. 88–89° C. | U.S. Pat. No. 2,993,891 |

Table 2-continued

| Compound No. | Chemical formula | Remarks |
|---|---|---|
| (v) | =CH—〇—NO$_2$ m.p. 196–197° C. | J. Heterocyclic Chemistry Vol. 2, 95 (1965) |
| (vi) | =CH—〇—Cl m.p. 151–152° C. | Z. Naturforsch 24B, No. 5, 651 (1969) |
| (vii) | =CH$_2$—〇—Cl b.p. 174–175° C/5 mmHg | German Patent 844,292 |
| (viii) | H$_3$C– =CH—〇—Cl m.p. 96–97° C. | homologue (prepared by the present inventors) |
| (ix) | H$_3$C– =CH—〇 | U.S. Pat. No. 2,993,891 and Monatsh 35, 311 (1914) |

EXAMPLE 1

Preventive activity on rice blast (*Pyricularia oryzae*)

When rice plants (var.: Kinki No. 33) were grown up to a 5-leaves stage in a flower pot of 9 cm. in diameter, an aqueous solution of each emulsifiable concentrate of the present compounds was sprayed thereon at the rate of 15 ml. per pot. After 1 day, the rice plants were inoculated with spraying of a spore suspension of *Pyricularia oryzae* and incubated at 25° C. in a humid, constant temperature chamber. After 4 more days, the disease severity was determined from a percentage of infecting leaf area to examine the preventive activity. The test results are as shown in Table 3. The disease severity and disease control were calculated according to the following equation.

$$\text{Disease severity} = \frac{\Sigma(\text{Infection index} \times \text{Number of leaves})}{8 \times \text{Total number of leaves observed}} \times 100$$

| Infection index | % of leaf area infected |
|---|---|
| 0 | 0 % (None) |
| 1 | Less than 10 % |
| 2 | 10 % to less than 25 % |
| 4 | 25 % to less than 55 % |
| 8 | 55 % – 100 % |

$$\text{Disease control} = \left(1 - \frac{\text{Disease severity in treated plot}}{\text{Disease severity in untreated plot}}\right) \times 100$$

Table 3

| Test compound | | Concentration of active ingredient (ppm) | Disease severity (%) | Disease control (%) | Phyto-toxicity |
|---|---|---|---|---|---|
| Present Comp. | 1 | 100 | 0 | 100 | no |
| " | 2 | 100 | 0 | 100 | no |
| " | 3 | 100 | 0 | 100 | no |
| " | 4 | 100 | 1.3 | 99 | no |
| " | 5 | 100 | 1.3 | 99 | no |
| " | 6 | 100 | 0 | 100 | no |
| " | 7 | 100 | 0 | 100 | no |
| " | 8 | 100 | 0 | 100 | no |
| " | 9 | 100 | 1.3 | 99 | no |
| " | 10 | 100 | 1.3 | 99 | no |
| " | 11 | 100 | 1.3 | 99 | no |
| " | 12 | 100 | 2.5 | 97 | no |
| " | 13 | 100 | 0 | 100 | no |
| " | 14 | 100 | 0 | 100 | no |
| Commercial fungicide | A* | 100 | 7.5 | 92 | no |
| Control | (i) | 500 | 100 | 0 | no |
| " | (ii) | 500 | 93.8 | 7 | no |
| " | (iii) | 500 | 90.0 | 10 | no |
| " | (iv) | 500 | 97.5 | 2 | no |
| " | (v) | 500 | 100.0 | 0 | no |
| " | (vi) | 500 | 100.0 | 0 | no |
| " | (vii) | 500 | 97.5 | 2 | no |
| " | (viii) | 500 | 91.3 | 9 | no |
| " | (ix) | 500 | 90.0 | 10 | no |
| Untreated plot | | — | 100.0 | 0 | |

Note*O,O-diisopropyl-S-benzylphosphorothioate

EXAMPLE 2

Curative activity on rice blast (*Pyricularia oryzae*)

When rice plants (var.: Kinki No. 33) were grown up to a 4-leaves stage in a flower pot of 9 cm. in diameter, the rice plants were inoculated with spraying of a spore suspension of *Pyricularia oryzae* and inculated at 25° C. in a humid, constant temperature chamber. Eighteen hours after the inoculation, the plants were taken out of the chamber and dried spontaneously at room temperature.

Then, an aqueous solution of each emulsifiable concentrate of the present compounds was sprayed on the dried plants at the rate of 15 ml. per pot. After the sprayed solution was dried, the plants were again placed in the chamber, and 3 days thereafter the disease severity was determined from a percentage of infecting leaf area appeared on the top leaves to examine the curative activity.

The test results obtained are as shown in Table 4. The disease severity and disease control were calculated in the same manner as described in Example 1.

Table 4

| Test compound | | Concentration of active ingredient (ppm) | Disease severity (%) | Disease control (%) | Phyto-toxicity |
|---|---|---|---|---|---|
| Present Comp. | 1 | 200 | 1.3 | 99 | no |
| " | 3 | 200 | 0 | 100 | " |
| " | 5 | 200 | 0 | 100 | " |
| " | 6 | 200 | 0 | 100 | " |
| " | 7 | 200 | 0 | 100 | " |
| " | 9 | 200 | 1.3 | 99 | " |
| " | 13 | 200 | 1.3 | 99 | " |
| " | 14 | 200 | 0 | 100 | " |
| Commercial fungicide | C* | 200 | 7.5 | 92 | " |
| " | B** | 20 | 17.5 | 82 | " |
| Control | (ii) | 500 | 97.5 | 0 | " |
| " | (iii) | 500 | 97.5 | 0 | " |
| Control | (iv) | 500 | 100.0 | 0 | no |
| " | (vi) | 500 | 100.0 | 0 | " |
| " | (vii) | 500 | 97.5 | 0 | " |
| Untreated plot | | — | 97.5 | 0 | |

Note*O-ethyl-S,S-diphenyl-phosphorodithiolate
**Kasugamycin hydrochloride

As clearly shown in Examples 1 and 2, the present compounds have a high preventive and curative activities on rice blast, are sufficiently worthy of a practical use compared with commercially available fungicides, and are extremely superior in a fungicidal activity to the control compounds. Therefore, the present compounds were examined on the inhibitory activity on mycelial growth of *Pyricularia oryzae in vitro*.

EXAMPLE 3

Inhibitory activity on mycelial growth of Pyricularia oryzae

A minimum inhibitory concentration (MIC) on mycelial growth of *Pyricularia oryzae* was obtained according to the agar dilution method. The test results are as shown in Table 5. The test method was as follows:

| | |
|---|---|
| medium : | agar medium containing the extract of straws of rice plant |
| inoculation: | mycelial disc (5 mm. in diameter) was inoculated in a center of the agar plate (triplicate) |
| incubation: | at 27° C. |
| measurement: | 2 weeks after inoculation, mycelial growth was examined and the average value of the longest and shortest diameters of the colony was calculated to obtain MIC. |

Table 5

| Test compound | | Diameter of mycelium (m/m) | | | | MIC (ppm) |
|---|---|---|---|---|---|---|
| | | 250 ppm | 50 ppm | 10 ppm | 2 ppm | |
| Present Comp. | 1 | 0 | 0 | 0 | 0 | <2 |
| " | 2 | 0 | 0 | 0 | 0 | <2 |
| " | 3 | 0 | 0 | 0 | 0 | <2 |
| " | 4 | 0 | 0 | 0 | 0 | <2 |
| " | 5 | 0 | 0 | 0 | ±** | ≈2 |
| " | 6 | 0 | 0 | 0 | 0 | <2 |
| " | 7 | 0 | 0 | 0 | 0 | <2 |
| " | 8 | 0 | 0 | 0 | 0 | <2 |
| " | 9 | 0 | 0 | 0 | ±** | ≈2 |
| " | 10 | 0 | 0 | 0 | ±** | ≈2 |
| " | 11 | 0 | 0 | 0 | ±** | ≈2 |
| " | 12 | 0 | 0 | 0 | 2.0 | ≧2 |
| " | 13 | 0 | 0 | 0 | ±** | ≈2 |
| " | 14 | 0 | 0 | 0 | ±** | ≈2 |
| Control | (ii) | ±** | 35.5 | 49.0 | 68.5 | ≈250 |
| " | (iii) | 11.0 | 40.0 | 55.0 | 65.0 | >250 |
| " | (iv) | ±** | 31.5 | 48.5 | 63.0 | ≈250 |
| " | (v) | 30.5 | 43.0 | 58.5 | 69.5 | >250 |
| " | (vi) | 3.0 | 34.5 | 51.5 | 66.0 | ≧250 |
| " | (vii) | ±** | 32.0 | 49.0 | 62.0 | ≈250 |

Table 5-continued

| Test compound | Diameter of mycelium (m/m) | | | | MIC |
| --- | --- | --- | --- | --- | --- |
| | 250 ppm | 50 ppm | 10 ppm | 2 ppm | (ppm) |
| " (viii) | 28.5 | 48.0 | 57.5 | 66.5 | >250 |
| Commercial fungicide C* | 0 | 0 | 2.0 | 37.5 | 50-10 |
| Diameter of mycelium in untreated plot: 63.5 m/m | | | | | |

Note*O-ethyl-S,S-dipheyl phosphorodithiolate
**±mycelial growth was observed on a discinoculum alone In the same manner as described in Example 3, several compounds of the present invention were tested on a lower concentration to obtain a MIC of 0.4 to 0.8 ppm. Therefore, it was found from the above example that the present compounds have a specific inhibitory activity on mycelial growth of *Pyricularia oryzae*, and have an incomparably higher activity than that of the homologues.

What is claimed is:

1. An α-Benzylidene-γ-butyrolactone derivative of the formula,

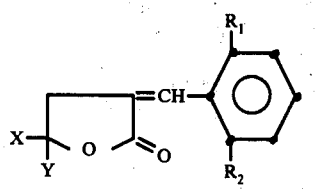

wherein $R_1$ and $R_2$ are, same or different, hydrogen, halogen and $C_1$–$C_4$ alkyl; X and Y are, same or different, hydrogen or $C_1$–$C_4$ alkyl; provided that both $R_1$ and $R_2$ are not hydrogen simultaneously, and $R_1$ and $R_2$ are not hydrogen and halogen respectively when both X and Y are hydrogen simultaneously.

2. An α-Benzylidene-γ-butyrolactone derivative according to claim 1, wherein $R_1$ is halogen, and $R_2$, X and Y are as defined in claim 1.

3. An α-Benzylidene-γ-butyrolactone derivative according to claim 1, wherein $R_1$ is halogen, X is $C_1$–$C_4$ alkyl and $R_2$ and Y are as defined in claim 1.

4. An α-Benzylidene-γ-butyrolactone derivative according to claim 1, wherein $R_1$ and X are $C_1$–$C_4$ alkyl, and $R_2$ and Y are as defined in claim 1.

5. A compound of the formula,

6. A compound of the formula,

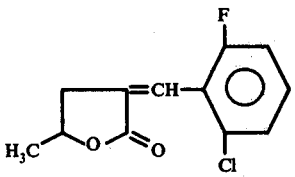

7. A compound of the formula,

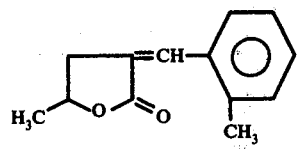

8. A compound of the formula,

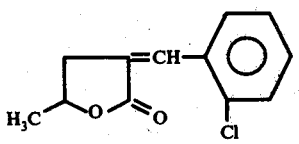

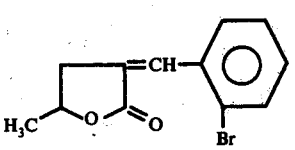

9. A fungicidal composition for application to plant fungi containing a fungicidal amount of an α-benzylidene-γ-butyrolactone derivative of claim 1 as an active ingredient and a solid or liquid carrier.

10. A fungicidal composition according to claim 9, wherein the amount of the active ingredient is 0.1 to 99.9% by weight based on the weight of the composition.

11. A method for controlling plant fungi which comprises applying an effective amount of an α-benzylidene-γ-butyrolactone derivative of claim 1 to the plant fungi.

* * * * *